United States Patent [19]

Freitag et al.

[11] Patent Number: 4,839,297
[45] Date of Patent: Jun. 13, 1989

[54] TEST CARRIER AND METHOD FOR THE ANALYTICAL DETERMINATION OF A COMPONENT OF A BODY FLUID

[75] Inventors: Helmut Freitag, Indianapolis, Ind.; Joachim Steinbiss, Darmstadt; Anselm Rothe, Birkenau, both of Fed. Rep. of Germany

[73] Assignee: Boehringer Mannheim GmbH, Mannheim, Fed. Rep. of Germany

[21] Appl. No.: 117,867

[22] Filed: Nov. 9, 1987

[30] Foreign Application Priority Data

Nov. 12, 1986 [DE] Fed. Rep. of Germany ....... 3638654

[51] Int. Cl.[4] ............................................ G01N 33/52
[52] U.S. Cl. .................................... 436/170; 422/55; 422/56; 422/58; 435/16; 435/17; 435/805
[58] Field of Search ............... 422/55, 56, 58; 435/26, 435/805, 16, 17; 436/170

[56] References Cited

U.S. PATENT DOCUMENTS

| | | | |
|---|---|---|---|
| 3,917,453 | 11/1975 | Milligan | 435/26 X |
| 3,933,594 | 1/1976 | Milligan | 422/55 X |
| 3,936,357 | 2/1976 | Milligan | 435/26 X |
| 3,992,158 | 11/1976 | Przybylowicz et al. | |
| 4,108,729 | 8/1978 | Mennen | 422/56 X |
| 4,223,089 | 9/1980 | Rothe | 422/56 X |
| 4,477,575 | 10/1984 | Vogel et al. | |

FOREIGN PATENT DOCUMENTS

3130749C2 2/1983 Fed. Rep. of Germany.
3523439A1 1/1987 Fed. Rep. of Germany.

Primary Examiner—Sidney Marantz
Attorney, Agent, or Firm—Armstrong, Nikaido, Marmelstein & Kubovcik

[57] ABSTRACT

The present invention provides a test carrier (1) for the analytical determination of a component of a body fluid with a base layer (2) and at least two planar test layers which, in the initial state of the test carrier, before carrying out the determination, are separate from one another but can be brought into contact with one another by external manipulation, wherein a first test layer (8) and a second test layer (10) are arranged on the base layer essentially next to one another but separated in the initial state by a gap, a contact element (11, 17, 18, 20) being provided which consists of a capillary-active material which is so dimensioned that it can bridge the gap (12) and which is so mounted and arranged that, in a first position, it cannot contact at least one of the test layers (8, 10) but, by external pressure, it can be brought into a second position in which it contacts both test layers in such a manner that a liquid exchange between the test layers is possible.

21 Claims, 2 Drawing Sheets

TEST CARRIER AND METHOD FOR THE ANALYTICAL DETERMINATION OF A COMPONENT OF A BODY FLUID

The present invention is concerned with a test carrier for the analytical determination of a component of a body fluid having a base layer and at least two planar test layers which, in the initial state of the test carrier, before carrying out a determination, are separate from one another but can be brought into contact with one another by external manipulation.

Whereas previously in the clinical laboratory, the concentration of, for example, the components of the blood were determined practically exclusively with the help of liquid reagents, in recent times, so-called carrier-bound tests have achieved increasing importance. In the case of these, the reagents are embedded in appropriate layers of a solid test carrier on to which a drop of the sample is applied. The reaction of sample and reagents leads to a detectable signal, especially to a colour change, which can be evaluated visually or with the help of an apparatus, mostly reflection photometrically.

Test carriers are frequently constructed as test strips which consist essentially of a longitudinal base layer of synthetic resin material and test fields applied thereon. However, test carriers are also known which are made as quadratic or rectangular platelets.

Most processes of clinical chemistry require a sequence of individual reaction steps to be carried out precisely. These reaction steps include, for example, obtaining serum or plasma, removing disturbing substances and finally carrying out one or more detection steps. In the case of each of these steps, in general, reagents must be added at a definite point of time and a precise reaction time maintained Especially in the case of immuno-chemical processes, as a rule, several precise reaction steps, adjusted to one another, are necessary.

In the initial period of the development, test carriers only had one test layer. Various reagents were there admittedly combined in such a manner that even complicated reaction sequences were possible but one-layer test carriers do not permit a chronologically defined course of several reactions following one another. This also applies similarly to test carriers in which several test layers are in contact with one another permitting a liquid exchange. Admittedly, the sample penetrates gradually from layer to layer through the test carrier but a precise definition of the contact times between the various test layers is here also not possible.

This has led to the development of the initially mentioned test carrier in which at least two test layers in the initial state, i.e. before carrying out an analytical determination, are separate from one another but are so arranged that, by external manipulation, for example manually, they can be brought into contact with another. Such test carriers are described, for example, in U.S Pat. No. 3,933;594 and in Federal Republic of Germany Pat. No. 3130749. In these cases, a test layer is present on a base carrier, a further test layer is fixed with one edge, beside the first-mentioned test layer, on the base carrier In the initial state, it stands obliquely from the base carrier so that it does not touch the first-mentioned test layer By external pressure, it can be pressed down like a flap on to the test layer fixed on the base layer so that, at this moment, a liquid passing over from one test layer into the other test layer is possible. This test construction is relatively simple but only permits a two-stage course of the reaction In U.S. Pat. No. 3,936,357, there is described a test carrier which makes possible a multi-stage course of the reaction. It possesses several test layers which are connected by hinges and which can be alternatingly brought into contact with one another by bending and reversing. However, these test carriers are complicated and require a complicated handling so that they are not very good for an evaluation with a measurement apparatus. Furthermore, because of the complicated construction, the production is extremely laborious Finally, for the initiation of a reaction step, in each case a pressure must be exerted on the test layers. This is not possible with all test layers.

Starting herefrom, the problem forming the basis of the present invention is to provide a better possibility of interrupting and starting the course of the reaction on a test carrier at a desired time point so that a chronologically defined reaction course of at least two and preferably at least three reaction steps is possible The test carrier is to be suitable for an evaluation with an appropriate apparatus with which it forms a system.

Thus, according to the present invention, there is provided a test carrier for the analytical determination of a component of a body fluid with a base layer and at least two planar test layers which, in the initial state of the test carrier, before carrying out the determination, are separate from one another but can be brought into contact with one another by external manipulation, wherein a first test layer and a second test layer are arranged on the base layer essentially next to one another but separated in the initial state by a gap, a contact element being provided which consists of a capillary-active material which is so dimensioned that it can bridge the gap and is so positioned and arranged that, in a first position, it cannot contact at least one of the test layers but, by external pressure, it can be brought into a second position in which it contacts both test layers in such a manner that a liquid exchange between the test layers is possible A test layer in the meaning of the present invention is any layer of a test carrier participating in any way in the course of the reaction. At least two test layers are arranged, in the test carrier according to the present invention, essentially next to one another on the base layer in such a manner that, in the initial state, i.e. before carrying out an analytical determination, they are separated by a gap. Essentially next to one another is to be understood to mean that the test layers, over by far the greater part of their surface, do not overlap. If they do not overlap at all, the gap runs vertically to the base layer between the test layers. However, the present invention also includes cases in which the test layers overlap slightly but the overlapping regions are separated by a gap running substantially parallel to the base layer.

The contact element consists of a capillary-active material, i.e. a material in which a liquid can be transported by capillary action. There are especially preferred fabrics, textiles, fleece or papers, i.e. structures consisting of fibres in which the liquid is transported by the hollow spaces between the fibres. However, other porous structures can also be used, such structures being described, for example, in U.S. Pat. No. 3,992,158 as so-called spreading layers.

The desired positioning and arrangement of the contact element on the test carrier can be accomplished in various ways. Thus, for example, it can stand permanently in connection with one of the test layers so that a liquid exchange between this test layer and the contact element is possible at any time In particular, in this case, it can also be an integrated component of this test layer.

According to a preferred embodiment, a bendable covering film is provided which bridges over one of the test layers like a flap. It is fixed hinge-like on the base layer on the side remote from the other test layer (thus far, similarly to U.S. Pat. No. 3,933,594). On the side facing the other test layer, the covering film extends so far that it at least partly overlaps and covers the contact element when it is moved towards the base layer by external pressure. A pressure is thereby also exerted on the contact element, i.e. the contact can be operated by means of the covering film, a contamination of the part of the apparatus with which the flap-like covering film is pressed downwardly thereby being avoided. This embodiment is especially advantageous when the measurement head of a reflection photometer, which is employed for the evaluation of the test carrier and forms a system with this, is simultaneously used for pressing on the covering film. Such an apparatus is described in European Pat. No. 0,129,220.

A further advantageous development of the present invention provides that, between the covering film and the test layer bridged over by it, there is arranged a third test layer in such a manner that it can only be brought into contact with the test layer bridged by the covering film making possibly a liquid exchange by external pressure on the covering film. This third test layer can, for example, be coated directly on to the under side of the covering film. However, a separate test layer between the covering film and the test layer bridged by this can also be provided.

The materials of the test layer and of the contact element (at least on the mutually contacting surfaces) are preferably so adapted to one another that the contact element adheres to the test layer in the moist state. As soon as the contact element is brought into contact with a test layer moistened through by the sample liquid, it soaks up completely because of its capillary-active properties and itself becomes moist. When, according to this preferred embodiment, it now adheres to the test layer, the liquid connection between the test layers remains even when the external pressure, with which the contact element is brought into contact between the test layers making possible a liquid exchange, is again removed. This embodiment is, as described in the following in more detail, especially advantageous in connection with the previously described embodiment with a covering film and a third test layer present below the covering film.

BRIEF DESCRIPTION OF THE DRAWINGS

The present invention will now be explained in more detail in the following on the basis of the embodimental examples shown schematically in the accompanying drawings, in which.

Figure 1:
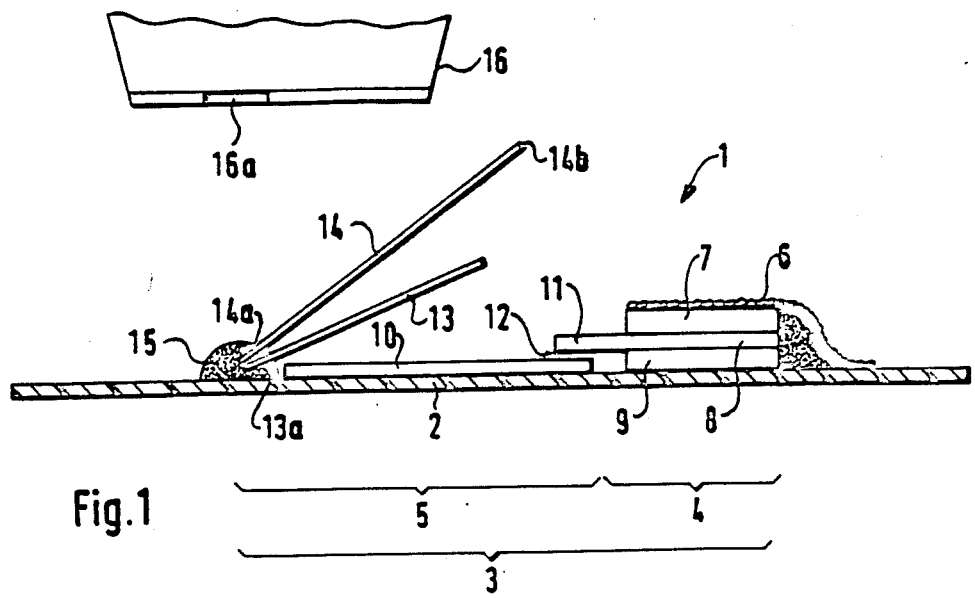
FIG. 1 is a cross-section of a test carrier according to the present invention in which the contact element is in its first position (contact opened)

The test carrier 1 illustrated in FIG. 1 has the principal form of a test carrier However, it is a very valuable analysis system which is scarcely comparable with previously known test strips. This test carrier is, apart from the particularities of the present invention, similar to the test carrier described in Federal Republic of Germany Patent No. 3523439.

On a base layer 2, there is present the actual test region indicated in totality by 3, which extends over only a part of the length of the base layer 2. The test region can be subdivided into a sample application zone 4 and into an evaluation zone 5.

In the sample application zone, there can be seen from above downwardly, a covering mesh 6, an erythrocyte separation layer 7, a first test layer 8 and a supporting layer 9.

A second test layer 10 is arranged essentially in the evaluation zone 5 on the base layer 2. The first test layer 8 and the second test layer 10 lie essentially next to one another but, in the case of the illustrated embodiment, overlap slightly. Preferably, the two layers overlap by at most about 30%. The region of the test layer 8 overlapping the test layer 10 forms the contact element 11. The contact element 11 is, in the case of the illustrated embodiment, thus an integral component of the test layer 8. Since the first test layer 8 is mounted on the supporting layer 9, the contact element 11, which continues the test layer 8 in a plane, is at a slight distance from the test layer 10, i.e. between the contact element 11 and the test layer 10, there is a gap 12. The material of the test layer 8 and of the contact element 11 is sufficiently stiff to maintain the distance between the contact element 11 and the test layer 10 so long as no external mechanical pressure is exerted from above on the contact element 11.

Over the second test layer 10 are arranged, in the evaluation zone, a third test layer 13 and a covering film 14. Both are fixed on one edge 13a or 14a with a melt adhesive strip 15 to the base layer 2. They are so stuck on that they run away obliquely from the base layer 2 Without use of external pressure, the test layer 10 does not come into contact with the third test layer 13.

Figure 2:
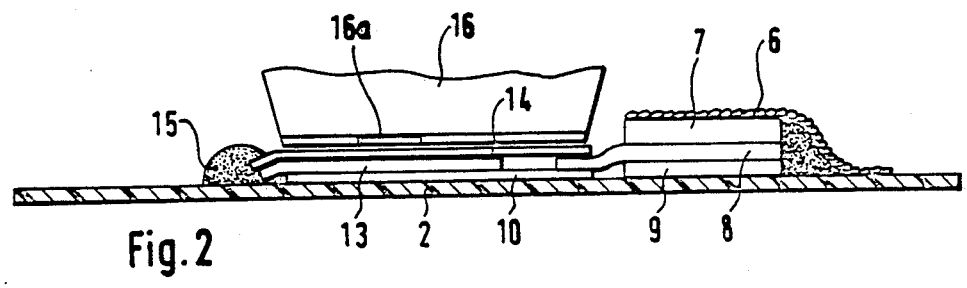
FIG. 2 is the test carrier according to FIG. 1 in which the contact is present in its second position (contact closed)

When, in the case of the illustrated test carrier according to the present invention, by external mechanical pressure, the covering film 14 is pressed downwardly in the direction of the base layer 2, then not only does the third test layer 13 come into contact with the second test layer 10 but, when the covering film is pressed down far enough, its end 14b facing the first test layer touches from above the contact element 11 and also presses this down on to the second test layer 10 so that the first test layer and the second test layer are in contact with one another making possible a liquid exchange. This is the second position of the contact element 11 (contact closed) which is illustrated in FIG. 2.

For carrying out an analysis, a drop of, for example, 30 $\mu$l. of blood is applied to the erythrocyte separation layer 7 (down through the protective mesh 6). The plasma penetrates through the erythrocyte separation layer 7, the erythrocytes thereby remaining behind so that only pure plasma gets into the first test layer 8. Because of the gap 12, a further passing over of the plasma into the second test layer is not possible, i.e. the liquid remains in a precisely predeterminable manner in the first test layer 8 until, by external pressure, the contact element 11 is pressed downwardly against the second test layer 10 and thus the gap between the first and second test layer is bridged by the capillary-active material of the contact element 11 The liquid can now pass over into the test layer 10.

In the test layer 10, the liquid again remains for a precisely predeterminable period of time until the flap-shaped covering film 14 is pressed down so that the third test layer 13 contacts the second test layer 10 and thus a further reaction step of the test can take place.

As mentioned above, the contact element 11 is preferably operated indirectly by pressing down the covering film 14 against the second test layer 10. In the illustrated embodiment, for this purpose, the covering film 14 is considerably longer than the third test layer 13 and extends so far in the direction of the first test layer 8 that, in the position illustrated in FIG. 2, it overlaps the contact element. This is especially preferred when the test carrier according to the present invention is used in a system with an appropriate evaluation apparatus which has an appropriate movable part with which the covering film 14 can be pressed downwardly. A single movable part of the apparatus can thus, via the covering film 14, press not only the contact element 11 but also the third test layer 13 against the second test layer 10. Such an apparatus is described in European Pat. No. 0,129,220. There, the measuring head of an appropriate reflection photometer is used as movable constructional part for the pressing. This is merely indicated in FIGS. 1 and 2 by reference numeral 16. The measurement head 16 has a measurement window 16a through which a reflection photometric measurement can take place The covering film 14 is preferably transparent in order to make possible the photometric evaluation of the colour reaction in the underlying layer.

In the case of the embodiment of the present invention illustrated in FIG. 1, it is especially advantageous when the contact element 11 consists of a material which, in a moist state, adheres to the second test layer 10 as soon as both have been brought into contact with one another by pressure. In this way, with only one operating element (for example the measurement head 16) of the evaluation apparatus, a three-stage reaction course can easily be achieved. If the flap-like covering film 14 is pressed down for the first time, then its end 14b presses the contact element 11 in this phase against the second test layer 10. Since the contact element 11 in this phase is moistened by the sample, it adheres to the test layer 10. Consequently, the liquid contact between the first test layer 8 and the second test layer 10 also remains when the measurement head 16 is again raised Since, in the case of this first pressing on of the covering film 14, the second test layer 10 is still dry, no passing over of liquid into the third test layer takes place. Only when a second reaction time has expired, in which the liquid has completely filled the second test layer 10 and the reaction provided for in this layer has taken place, is the measurement head 16 again lowered so that the covering film 14 and the third test layer 13 are again pressed against the second test layer 10. Since this is now wet, the liquid passes over into the third test layer and the reaction provided for in this test layer can take place.

The material of the contact element 11 is of considerable importance for its dependable function. On the one hand, in the dry state it must be sufficiently stable to prevent a premature contact with the second test layer 10. On the other hand, in the moistened state, it must be sufficiently flexible and contactable in order, in the downwardly pressed state, to be able to adhere dependably to the test layer 10 in order that the liquid transport is uniformly possible over the complete breadth of the test layer. Surprisingly, a number of materials fulfill these requirements. In particular, thin papers, fleece of various composition, thin fabrics and thin layers of porous synthetic resin have proved useful.

The test element according to the present invention is especially preferred for carrying out immunological determinations. If, for example, an antigen contained in a sample is to be determined, then, in the first test layer 8, there is present an enzyme-labelled antibody which is soluble in the sample liquid for this antigen. It is dissolved by the sample during a first reaction time and incubated with this so that the antigen binds specifically with the antibody. After this procedure, the test layer 8 contains complexes of sample antigen and enzyme-labelled antibody, as well as non-bound, enzyme-labelled antibody.

After pressing down of the contact element 11, these components pass over with the sample liquid into the second test layer 10 in which is present, in carrier-fixed form, an antigen for the antibody from the first test layer. During a second reaction time, the non-complex antibody is bound to the carrier-fixed antigen The complexes, on the other hand, remain mobile On the third test layer 13, there is present a substrate for the enzyme. If this test layer, for the initiation of a third reaction step, is pressed downwardly against the second test layer, then the freely mobile, enzyme-labelled antigen-antibody complexes pass over into the substrate-containing test layer 13. The enzyme catalyses a reaction of the substrate which, in known manner, leads to a detection signal and especially to a colour change of the layer 13.

The described course of an immunological test is known for analytical determinations as the so-called IEMA test. It can also be used for the determination of an antibody in the sample, in which case, in the previously described course of reaction, in each case antibody and antigen are to be exchanged. Hitherto, this test principle could not be carried out with the desired exactitude on test carriers because it is a prerequisite that the different reaction steps take place sharply separated from one another and, only after the taking place of the particular reaction step, is the passing over into the test layer possible in which the reaction components of the next reaction step are present. Consequently, such a determination is a very good example of the special advantageousness of the multi-stage course of the test on a test carrier which is now possible according to the present invention.

Figure 3:
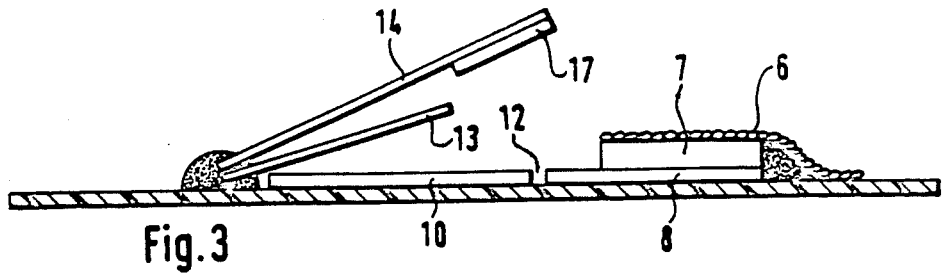
FIGS. 3-5 show three further different embodiments of a test carrier according to the present invention in cross-section.

FIG. 3 shows an embodiment in which the contact element 17 is not an integral part of one of the test layers. It is made of a layer of capillary-active material which is fixed on the end of the covering film 14 in such a manner that it overlaps the gap 12 between the test layers 8 and 10 when the covering film 14 is pressed downwardly against the test layers. The contact element can be so securely fixed on the covering film that it again lifts off with this from the test layers when pressure is no longer exerted on the covering film. Preferably, however, it is only lightly attached to the covering film, for example with a water-soluble adhesive, and consists of a material adhering to the test layers in the moist state. In this case, the contact element 17 remains in contact with the test layers even when it is no longer pressed on from above and, consequently, the covering film 14, because of its inherent elasticity, again lifts off from the test layers and the contact element.

Figure 4:
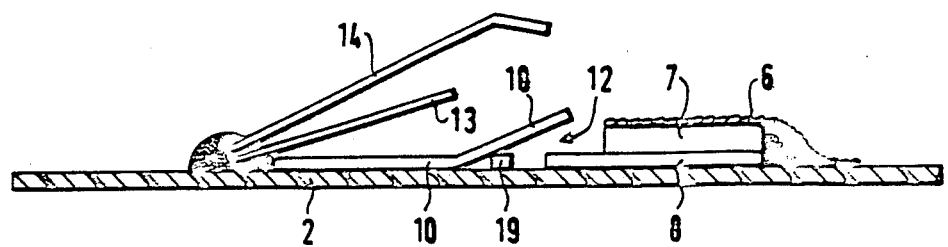

FIG. 4 shows a test carrier in which the contact element 18 is an integral component of the second test layer 10. Furthermore, there is provided an additional support element 19 between the contact element 18 and the base layer 2. It is thereby especially ensured that the contact element 18 first comes into contact with the first test layer 8 when it is pressed downwardly by external mechanical pressure.

Figure 5:
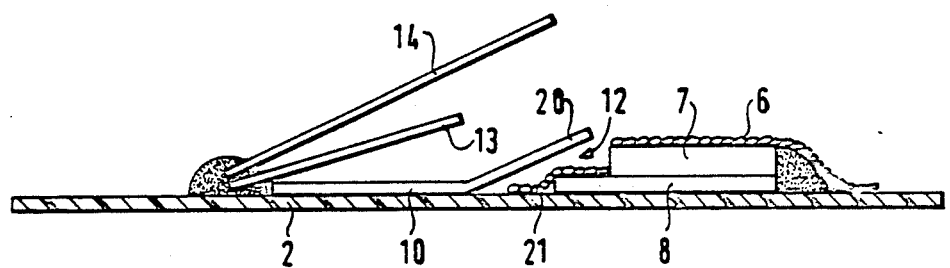

In the embodiment of the test carrier illustrated in FIG. 5, between the contact element 20, which in this case is an integral component of the test layer 10, and the test layer 8, there is arranged a hydrophobed mesh or fabric layer 21. Such a kind of construction proves to be favorable in cases in which first, in the case of an increased mechanical pressure on the contact element 20, there is to be achieved a liquid passing over from the first test layer 8 to the second test layer 10.

The following Examples are given for the purpose of illustrating the present invention:

EXAMPLE 1

Test strips for the measurement of N-acetyl-beta-D-glucosaminidase (NAG)

A test strip is constructed according to FIG. 1:
Test layer 8: 6×8 mm.×about 0.1 mm. thick.

Long-fiber paper (Schoeller & Hoesch, Gernsbach, Federal Republic of Germany) is impregnated with 0.2M citrate buffer (pH 4.9).

Test layer 10: 6×10 mm.×about 0.09 mm. thick.

Tea bag paper 212 (Schoeller & Hoesch, Gernsbach, Federal Republic of Germany) is impregnated with a 0.05M solution of p-nitrophenyl-N-acetylglucosaminide in 0.1M citrate buffer (pH 4.9).

Test layer 13: 6×8 mm.×about 0.08 mm. thick.

Nylon fabric 20 HC (Schweizer Seidengazefabrik, Thal, Switzerland) is impregnated with a 0.5M aqueous potassium carbonate solution.
Base layer 2

About 0.45 mm. thick polyester foil (Lonza, Weil, Federal Republic of Germany)
Erythrocyte separation layer 7

About 0.4 mm. thick glass fiber layer (Binzer, Hatzfeld, Federal Republic of Germany). The use of such glass fiber layers for erythrocyte separation is described in commonly assigned U.S. Pat. No. 4,477,575.
Covering film 14: 6×12 mm.

About 0.2 mm. thick polycarbonate foil (Lonza, Weil, Federal Republic of Germany).
Construction Gap 12 was at least 0.05 mm. wide. The overlap of layers 8 and 10 was about 1 mm.
Measurement procedure:

30 μl. NAG-containing sample solution are applied. A residence time of 90 seconds in reagent carriers 7 and 8 serves for the tempering necessary for the enzymatic reaction and for the adjustment of the acidic pH needed for the NAG. After pressing on of the covering film 14, a 2 minute reaction begins in the test layer 10. In the case of renewed pressing on of the covering film 14, rebuffering takes place. The p-nitrophenolate liberated proportionally to the amount of NAG can be measured remission photometrically.

EXAMPLE 2

Test strip for the measurement of theophylline in blood.
A test strip is constructed according to FIG. 4:
Test layer 8: 6×8 mm.

About 0.2 mm thick glass fiber paper P 300 (Binzer, Hatzfeld, Federal Republic of Germany) is impregnated with a 20 KU/l solution of a 3:1 $F_{ab}$-beta-galactosidase conjugate against theophylline.

Test layer 10: 6×11 mm.×about 0.25 mm. thick.

By immune precipitation according to European Patent Application No. 0,185,372 with anti-$F_c$ (sheep) antibody, a 1:8 IgG (sheep)-theophylline conjugate (polyhapten) is immobilized in a CS-104 cellulose/polyester mixed fleece (Boehringer Mannheim GmbH, Mannheim, Federal Republic of Germany).
Test layer 13: 6×8 mm.

Tea bag paper 212 (Schoeller & Hoesch, Gernsbach, Federal Republic of Germany) is impregnated with a 10 mM solution of chlorophenol red-beta-galactoside in phosphate buffered saline, pH 7 (PBS).
Base layer 2
Same as in Example 1.
Erythrocyte separation layer 7
Same as in Example 1.
Support element 19: 1×6 mm.×0.5 mm. thick.
Polyester layer located 2 mm. from test layer 8.
Measurement procedure:

30 μl. of theophylline-containing blood are pipetted on to the erythrocyte separation layer 7. After a first reaction time of 3 minutes in the tempered measurement apparatus, the covering film 14 is briefly pressed down and the contact operated by pressure on the contact element 18. The following liquid transport (chromatography) along the test layer 10 lasts 1 minute The covering film 14 is now finally pressed on and the still free amount of $F_{ab}$-galactosidase proportional to the theophylline content is determined by remission photometric measurement.

EXAMPLE 3

Test strip for the measurement of creatine kinase (CK) in blood, with inhibition of myokinase.

The test strip is constructed according to FIG. 5:
Test layer 8: 6×8 mm.×about 0.13 mm. thick.

Multifilar nylon fabric 4F (Schweizer Seidengazefabrik, Thal, Switzerland) is impregnated with a 1 mM solution of diadenosine pentaphosphate and 0.1 mM adenosine monophosphate.

Test layer 10: 6×11 mm.×about 0.37 mm.

Mixed fleece Lutrabond 3670 (Faserprodukte Lahnstein, Lahnstein, Federal Republic of Germany) is impregnated with a 3 mM solution of N-acetylcysteine and 80 mM creatine phosphate.

Test layer 13: 6×8 mm.×about 0.09 mm. thick.

Tea bag paper 212 (Schoeller & Hoesch, Gernsbach, Federal Republic of Germany) is impregnated with a solution containing 0.7 mM of adenosine diphosphate, 10 mM of glycerol, 100 KU/l of glycerokinase, 300 KU/l of peroxidase, 30 KU/l of glycerol-3-phosphate oxidase and 4 mM of ABTS (azino-di-[3-ethyl-benzthiazoline-sulphonate-6]. The hydrophobic fabric was a monofilar nylon fabric 21 NY 150 HC (Schweizer Seidengazefabrik, Thal, Switzerland).
Base layer 2.
Same as in Example 1.
Erythrocyte separation layer 7
Same as in Example 1.
Measurement procedure:

30 μl. of CK containing blood are pipetted on to the erythrocyte separation layer 7. During a first reaction time of 60 seconds in the tempered measurement apparatus, the myokinase inhibition takes place on reagent carrier 1. After pressing on of the covering film 14, the hydrophobic carrier is overcome and the CK is activated in test layer 10. After renewed pressing on of the flap, the remission photometric detection of the CK takes place.

In each of the working examples, the reactants are reacted at an appropriate temperature to bring about the desired reaction. Room temperature was used and is preferred but higher and lower temperatures can be utilized, depending upon the particular components and reaction conditions involved.

What is claimed is:

1. Test carrier assembly for the analytical determination of a component of a body fluid, comprising a base layer and at least two planar test layers which, in the initial state of the assembly, before the determination is carried out, are separate from one another but can be contacted by external manipulation, wherein a first test layer and a second test layer are arranged on the base layer essentially next to one another but separated by a gap, and a capillary-active material contact element is movable between two positions, an initial position and a contacting position, with the initial position being located so that the contact element does not contact at least one of the test layers, and the contacting position being such that upon the application of external pressure the contact element assumes the contacting position to bridge the gap and contacts both test layers to permit liquid exchange thereinbetween.

2. Test carrier assembly of claim 1, additionally including a bendable covering film overlying said second test layer in a flap-like manner and fixed to the base layer on the side facing away from the first test layer, and at least partly covering the contact element when brought into contact by external pressure with the second test layer.

3. Test carrier assembly of claim 2, wherein the contact element is initially attached to the covering film.

4. Test carrier assembly of claim 2, wherein a third test layer is located between the covering film and the second test layer, said third test layer only initially contacting the second test layer to make liquid exchange therebetween possible when pressure is applied to the covering film.

5. Test carrier assembly of claim 1, wherein when the contact element is in the contacting position and is moistened by the sample liquid, it adheres to said first and second test layers.

6. Test carrier assembly of claim 1, wherein in the initial position the contact element contacts one of the first and second test layers, making a liquid exchange between that test layer and the contact element possible, and the contact element partly overlaps without contacting the other of the first and second test layers.

7. Test carrier assembly of claim 6, wherein the contact element is an integral component of the test layer which it contacts in the initial position.

8. Test carrier assembly of claim 1, wherein a contact element support is provided between the first and second test layers.

9. Test carrier assembly of claim 1, additionally including a hydrophobic layer arranged in the region of the gap to be in the contacting position between the contact element and at least one of the first and second test layers, with liquid exchange between the contact element and the test layer contacting the hydrophobic layer possible only upon the application of increased external pressure upon the contact element.

10. Test carrier assembly for the analytical determination of a component of a body fluid, comprising a base layer, at least two test layer means for performing steps of the analytical determination on the body fluid, with at least one of said test layer means performing a step which leads to a detectable signal which can be evaluated for the analytical determination of said component, wherein a first test layer means and a second layer means are located on the base layer proximate each other but separated by a gap, and contact element means located initially so that the contact element means does not contact at leas one of the first and second test layer means, and movable from the initial location to a second location by the application of external pressure to bridge the gap and to contact both of the first and second test layer means, said contact element means for transferring liquid by capillary action from one of the first and second test layer means to the other when in the second location.

11. Test carrier assembly of claim 10, wherein in the initial location the contact element means contacts one of the first and second test layer means.

12. Test carrier assembly of claim 11, wherein the contact element means is an integral component of the contacted one of the first and second test layer means.

13. Test carrier assembly of claim 10, further including a bendable covering means which overlies at least part of the second test layer means and is fixed at one edge to the base layer at a location on the opposite side of said second test layer means from said first test layer means, said covering means for transmitting pressure from an external source to said contact element means and for reducing contamination of the test carrier assembly.

14. Test carrier assembly of claim 13, wherein the covering means is for transmitting pressure from the measuring head of a reflection photometer to the contact element means to cause the contact element means to bridge the gap and to contact both of the first and second test layer means.

15. Test carrier assembly of claim 10, further including a third test layer means overlying the second test layer means for forming said detectable signal when contacting the second test layer means with resultant liquid exchange from the second test layer means to the third test layer means.

16. Test carrier of claim 15, further including a bendable covering means which overlies at least part of the second test layer means for transmitting pressure from an external source to said contact element means and for reducing contamination of the test carrier assembly.

17. Test carrier assembly of claim 16, wherein the third test layer means is coated on the side of the covering means facing the second test layer means.

18. Test carrier of claim 16, wherein the covering means is movable from an initial position wherein the covering means does not contact a test layer means to a second position wherein the covering means contacts at least part of the third test layer means and at least part of the contact element means.

19. Test carrier assembly of claim 16, wherein when wetted by liquid exchange the contact element means adheres to the test layer means from which the liquid is exchanged.

20. Test carrier assembly of claim 19, wherein initially the contact element means is fixed to the covering means.

21. A method for the analytical determination of a component of a body fluid, said method comprising forming in a first test layer of a test carrier an unbound complex of said component and a first agent complexable therewith which is present in excess in the first test layer by applying a predetermined amount of said body fluid to the first test layer and maintaining the component and the first agent under complexing conditions for a predetermined time, thereafter applying external pressure to a capillary-active contact element to cause the first test layer and a second test layer to both be contacted by the contact element to cause liquid exchange between the first and second test layers, and binding excess first agent to said second test layer by complexing said first agent with a second agent which is complexable therewith and is bound to said second test layer, and thereafter, after a predetermined time, producing a detectable signal which can be evaluated for the analytical determination of the component by causing a reaction between the unbound complex and a reactant to produce said detectable signal by contacting the second test layer with a third test layer which contains said reactant to cause liquid exchange from the second test layer to the third test layer, and thereafter evaluating the detectable signal to determine said component.

* * * * *